United States Patent [19]
McGurk-Burleson et al.

[11] Patent Number: 4,811,734
[45] Date of Patent: Mar. 14, 1989

[54] SURGICAL CUTTING INSTRUMENT

[75] Inventors: Erin McGurk-Burleson, Clemente, Calif.; Elmer Koehler, St. Louis, Mo.; Victor Packham, Santa Ana, Calif.

[73] Assignee: Baxter Travenol Laboratories, Inc., Deerfield, Ill.

[21] Appl. No.: 85,644

[22] Filed: Aug. 13, 1987

[51] Int. Cl.⁴ ............................................. A61B 17/32
[52] U.S. Cl. .................................... 128/305; 30/29.5; 30/240
[58] Field of Search ............... 128/305, 312, 313, 318, 128/751, 755; 604/22; 30/264, 240, 29.5, 347

[56] References Cited

U.S. PATENT DOCUMENTS

| | | | |
|---|---|---|---|
| D. 219,252 | 11/1970 | Bogoff | D24/03 |
| D. 275,127 | 8/1984 | Edwards | D24/26 |
| 2,729,210 | 1/1956 | Spencer | 128/2 |
| 3,618,611 | 11/1971 | Urban | 128/305 |
| 3,815,604 | 6/1974 | O'Malley et al. | 128/305 |
| 3,945,375 | 3/1976 | Banko | 128/6 |
| 3,990,453 | 11/1976 | Douvas et al. | 128/305 |
| 4,099,529 | 7/1978 | Peyman | 128/305 |
| 4,111,207 | 9/1978 | Seiler Jr. | 128/305 |
| 4,203,444 | 5/1980 | Bonnell et al. | 128/276 |
| 4,274,414 | 6/1981 | Johnson et al. | 128/305 |
| 4,598,710 | 7/1986 | Kleinberg et al. | 128/318 |
| 4,603,694 | 8/1986 | Wheeler | 128/312 |

FOREIGN PATENT DOCUMENTS 452936 11/1948 Canada ............................ 30/29.5
1067176 10/1959 Fed. Rep. of Germany ........ 604/22

OTHER PUBLICATIONS

*Arthroscopic Surgery Blades*, Dyonics, Inc., R-86 7129 Rev.-B8M (1986).
*New and Controversial Aspects of Vetreoretinal Surgery*, "The Visc and the Vitreomicroscope", Jean-Marie Parel, C.V. Mosby Co., St. Louis (1977).

*Primary Examiner*—Andrew M. Dolinar
*Attorney, Agent, or Firm*—Gordon L. Peterson

[57] ABSTRACT

A surgical cutting instrument comprising an outer tube having a peripheral wall and a longitudinal axis. The outer tube has a plurality of openings arranged generally longitudinally along the outer tube. Each of the openings has first and second cutting edges defining portions of the periphery of such opening. Each of the first cutting edges is substantially straight as viewed in a particular direction perpendicular to the longitudinal axis of the outer tube. An inner cutting member to rotatable within the outer tube. The inner cutting member has a cutting edge cooperable with the first and second cutting edges of the openings of the outer tube for cutting material from within the patient with a shearing action.

19 Claims, 2 Drawing Sheets

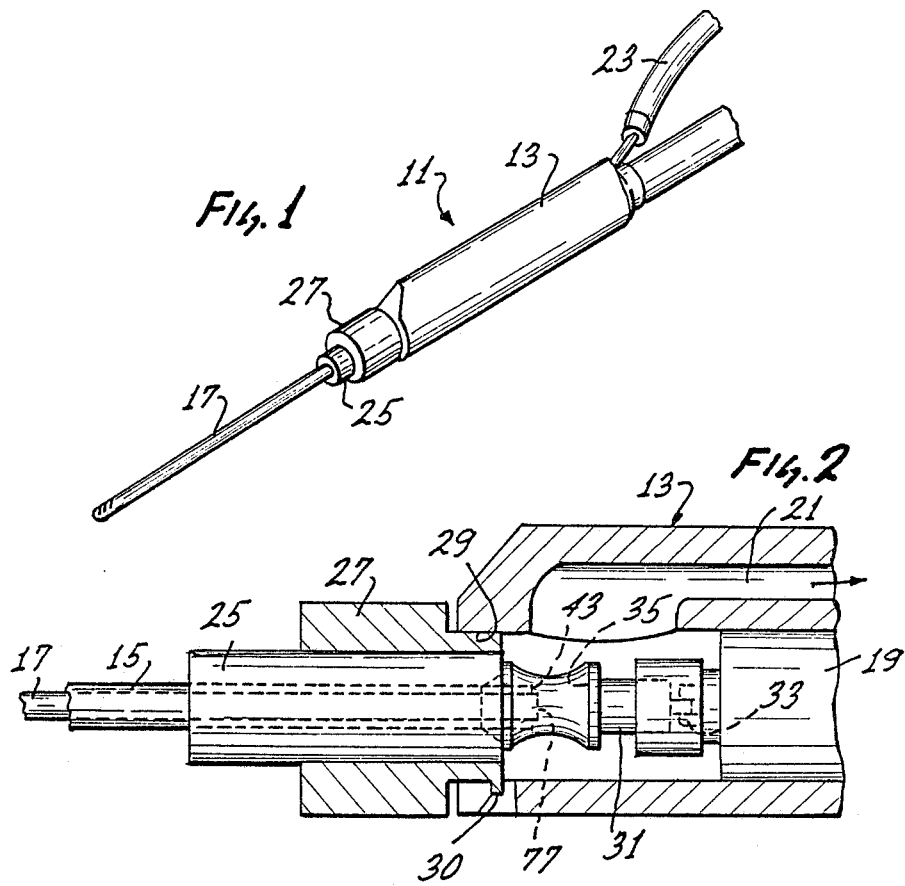
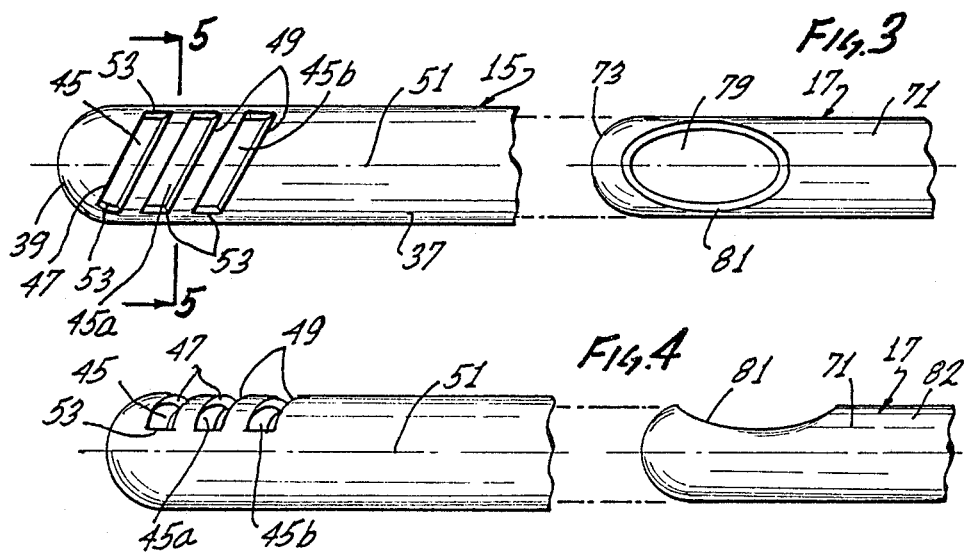

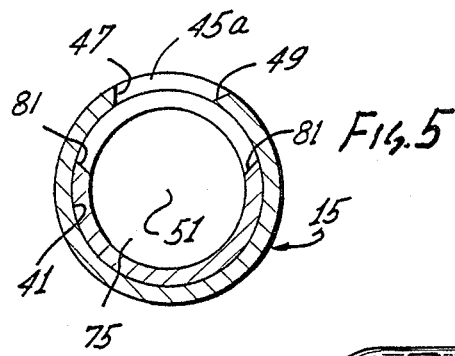
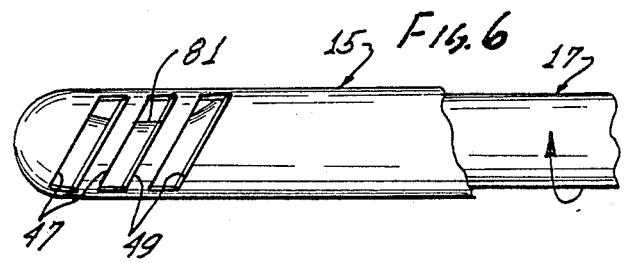
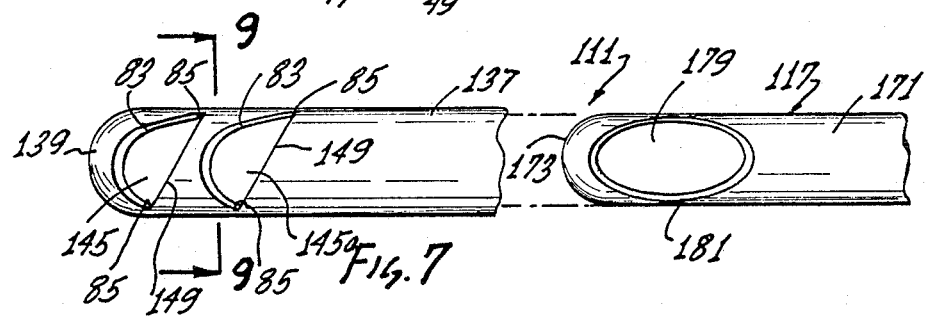
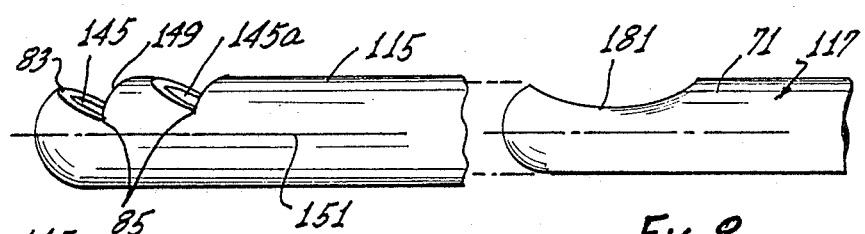
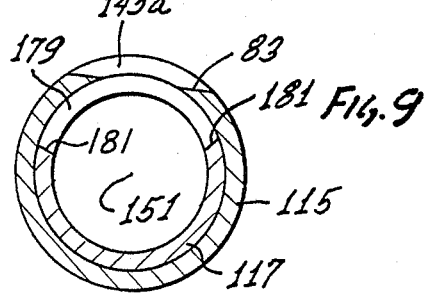
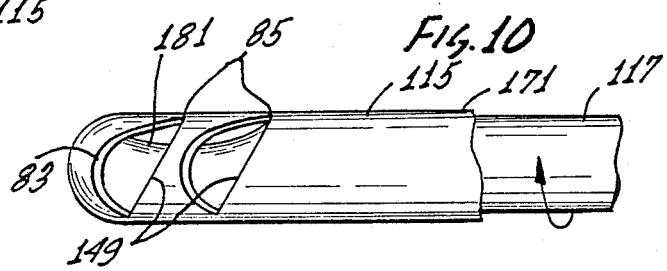

SURGICAL CUTTING INSTRUMENT

BACKGROUND OF THE INVENTION

This invention relates to a surgical cutting instrument of the type employing rotary cutters. Instruments of this type are usable for various surgical procedures in various regions of the body, such as in the eye and knee. For example, the surgical cutting instrument may be inserted through a small opening into the knee joint and used for cutting the meniscus or other soft or hard material or tissue.

Generally, a surgical cutting instrument of this type includes an outer tube having a peripheral wall, an end wall, an opening in one or both of the peripheral wall and the end wall and a cutting edge defining at least a portion of the periphery of the opening. An inner cutting member, which may also be in the form of a tube, rotates or translates within the outer tube. The inner cutting member has a cutting edge that cooperates with the cutting edge of the outer tube for cutting material with a shearing action as the inner cutting member is moved relative to the outer tube. One surgical cutting instrument of this general type is shown and described in Johnson et al U.S. Pat. No. 4,274,414.

Another cutting instrument of this type is the whisker cutter. In this instrument, the outer tube has a plurality of small circular openings to adapt the instrument for cutting fine hair-like projections, such as synovial tissue, from within the knee. While the whisker construction is satisfactory for certain applications, it is not suitable for a broader range of applications. For example, the round edges of the circular small holes of the outer tube do not provide as good a scissors or shearing action as is desirable for some applications. In addition, the small holes also make the outer tube not particularly satisfactory for use as a curette.

Notwithstanding a proliferation of known configurations for the outer tube and the inner cutting member, there are problems with poor cutting ability and inconsistent quality. In addition, poor cutting can lead to clogging of the instrument.

SUMMARY OF THE INVENTION

This invention provides a novel surgical cutting instrument having various different features which tend to solve the problems identified above. With this invention, the surgical cutting instrument is adapted for multiple applications, and the outer tube can serve a scraping function like a curette. In addition, cutting ability and quality are improved, and the likelihood of clogging is reduced.

According to one feature of the invention, the outer tube has a plurality of openings which provide multiple opportunities for cutting of material. However, the openings are substantially larger than the small-diameter circular openings of the whisker cutter, and consequently, this surgical cutting instrument can also serve like a curette in cutting and scraping tissue as the outer tube of the instrument is moved generally axially.

Another important feature of the multiple openings is that each of the openings has first and second cutting edges defining portions of the periphery of such opening, with the first cutting edge being substantially straight as viewed in a particular direction perpendicular to the longitudinal axis of the outer tube. The use of an edge which is straight when viewed in this direction enhances the scissor-like or shearing action obtainable with the surgical cutting instrument. This shearing action can be further enhanced by having the first edge extend circumferentially of the outer tube at an acute angle relative to a radial plane. Of course, these features and characteristics can be employed in one or more of the openings. Preferably, the openings are substantially identical.

In a preferred construction, the straight edge and the opening extend circumferentially of the outer tube for at least about 90 degrees. The straight edge may optionally define a proximal edge of the associated opening.

According to one preferred embodiment, each of the openings includes a curved edge, which includes the second edge. The straight edge intersects the associated curved edge and substantially defines therewith the full periphery of the associated opening. The curved edge is preferably part oval as viewed in a direction perpendicular to the longitudinal axis of the outer tube.

In order to provide a sufficiently large opening so that the outer tube can better serve a curette-like function, the ratio of the length of the periphery of each opening to the outside diameter of the outer tube is at least about 1.5 to 1. If the ratio is less than this, use of the outer tube as a curette may be impaired. Although a ratio of over 1.5 to 1 is known for a single opening and for one of a multiplicity of openings, this ratio has not been employed heretofore for each of a plurality of longitudinally arranged openings. Preferably, to enhance the ability of the outer tube to serve as a curette, this ratio should be at least about 2 to 1, and for still improved results, the ratio can be in the range of 2.3 to 3.4 and greater to 1.

The ability of the outer tube to serve as a curette in response to axial motion can be enhanced by arranging the openings longitudinally on the outer tube and by lengthening the circumferential extent of the openings. In this regard, the opening preferably extends circumferentially of the outer tube for at least about 90 degrees to thereby lengthen the cutting edge in a direction generally transverse to the longitudinal axis of the outer tube.

In another preferred form of the invention, each of the second edges is also substantially straight as viewed in a direction perpendicular to the longitudinal axis of the outer tube. The first and second edges can advantageously extend circumferentially, and the openings are preferably elongated circumferentially or in the direction of the first and second edges.

In one preferred construction, the first and second cutting edges intersect to form a corner, and the shearing action progresses along both of the cutting edges toward the corner. The corner tends to trap material to be cut and prevent its escape to thereby increase the cutting ability of the instrument and make the results more consistent. This feature may be present in one or more of the openings of the outer tube.

The inner cutting member can be tubular or nontubular so long as it provides a cutting edge that cooperates with the cutting edges of the openings of the outer tube. Preferably, however, the inner cutting member includes an inner tube having an opening therein, with the cutting edge of the inner tube extending along the periphery of the opening. Although the opening can be of various different configurations, one preferred configuration is oval because an oval opening can be used with a multiplicity of different opening configurations of the outer tube.

BRIEF DESCRIPTION OF THE DRAWINGS

FIG. 1 is an isometric view of a surgical cutting instrument constructed in accordance with the teachings of this invention.

FIG. 2 is an enlarged fragmentary sectional view illustrating the coupling of the outer tube and the inner cutting member to the handle.

FIG. 3 is a fragmentary, exploded top plan view of the distal regions of the inner and outer tubes.

FIG. 4 is a side elevational view of the construction shown in FIG. 3.

FIG. 5 is an enlarged sectional view taken generally along line 5—5 of FIG. 3.

FIG. 6 is a top plan view of the distal region of the surgical cutting instrument showing how the cutting edges cooperate to cut material.

FIGS. 7 and 8 are top plan and side elevational views, respectively, similar to FIGS. 3 and 4, respectively, illustrating a second embodiment of the invention.

FIG. 9 is an enlarged sectional view taken generally along line 9—9 of FIG. 7, with the inner tube being fully inserted into the outer tube.

FIG. 10 is a top plan view of the distal region of the surgical cutting instrument showing how the cutting edges cooperate to cut material.

DESCRIPTION OF THE PREFERRED EMBODIMENTS

FIGS. 1–6 show a surgical cutting instrument 11 which generally comprises a handle 13, an outer tube 15, and an inner cutting member in the form of an inner tube 17. The inner tube 17 is slidably receivable and rotatable within the outer tube 15. The outer tube 15 is fixedly attached to the handle 13 in a known manner, and the inner tube 17 is drivable by a motor 19 carried by the handle 13. The handle 13 also provides a passage 21 which is coupled by a conduit 23 (FIG. 1) to a vacuum source (not shown) for applying suction pressure to the interior of the inner tube 17 to withdraw material severed during operation of the cutting instrument.

More specifically and by way of example, a sleeve 25 is suitably fixedly attached to the outer tube 15, and the sleeve in turn is releasably mounted on a collar 27 in a conventional manner, such as by ball detents and a key and key way (not shown). The collar 27 is removably received within a bore 29 of the handle 13 by a conventional quick disconnect connection 30. The inner tube 17 extends proximally of the sleeve 25 where it is coupled by a conventional coupling 31 to a drive shaft 33 (FIG. 2) of the motor 19. With this construction, the motor 19 can rotate the inner tube 17 within the outer tube 15 in a known manner. Vacuum pressure may be applied to the interior of the inner tube 17 via the passage 21 and a radial opening 35 in the coupling 31 in a conventional manner. The bearing support for the rotation of the inner tube 17 can be provided in whole or in part by the outer tube 15 or in any other suitable manner known in the art.

The outer tube 15 is sized for insertion through an opening, such as a puncture or incision, in a patient. For example, the outer tube may be sized for insertion through an opening in the knee and may be used, for example, for cutting synovial tissue in the knee.

The outer tube 15 has a peripheral wall 37 and an end wall 39 at a distal end of the outer tube. Although various configurations are possible, the peripheral wall 37 is preferably cylindrical, and the end wall, in this embodiment, is preferably generally hemispherical and of the same radius as the peripheral wall. The outer tube 15 has a passage 41 (FIG. 5) which extends completely through the outer tube from a proximal end 43 (FIG. 2) all the way to the end wall 39 at the distal end of the outer tube. The passage 41 is cylindrical throughout the full length of the peripheral wall 37 and is hemispherical within the hemispherical end wall 39.

The outer tube 15 has openings 45, 45a and 45b. This invention differs from the prior art in that the outer tube 15 has multiple openings 45, 45a and 45b of a particular configuration and orientation and in the manner in which these openings cooperate with the inner tube 17. Although the openings 45, 45a and 45b could be of different configurations, in this embodiment, the openings are substantially identical. The openings are arranged longitudinally along the outer tube 15 with the opening 45 being the most distal. The openings 45a and 45b lie entirely in the peripheral wall 37, and the opening 45 lies primarily in the peripheral wall and partially in the end wall 39.

Each of the openings 45–45b has axially spaced, cutting edges 47 and 49 defining substantial portions of the periphery of the associated opening. At least one of the edges 47 and 49 of each of the openings 45–45b and, preferably both of such edges, is substantially straight as viewed in a particular direction perpendicular to a longitudinal axis 51 of the outer tube 15. As shown in FIG. 3, this particular direction is a top plan view looking directly down on the openings 45–45b. The edges 47 and 49 of the opening 45 are parallel, and preferably all of these edges are parallel.

The edges 47 and 49 of each of the openings 45–45b are joined by relatively short, axial cutting edges 53. The cutting edges 47 form the distal edges of each of the associated openings 45–45b, and the cutting edges 49 form the proximal edges of such openings. The axial edges 53 are straight as viewed in FIG. 3, except that the lower (as viewed in FIG. 3) axial edge 53 of the opening 45 is curved slightly because of its presence in the hemispherical end wall 39. Except for the curvature of this one cutting edge 53, the openings 45–45b are completely identical, and the curvature of this one cutting edge 53 does not keep the openings 45–45b from being substantially or essentially identical.

At least one, and preferably both, of the cutting edges 47 and 49 of each of the openings 45–45b extend circumferentially of the outer tube 15 at an acute angle relative to a radial plane as shown in FIG. 3. In addition, at least one, and preferably all, of the openings 45–45b extend circumferentially of the outer tube 15 for at least 90 degrees, and in this embodiment, the openings extend circumferentially for less than 180 degrees and about 160 degrees. This lengthens the cutting edges 47 and 49.

Each of the openings 45–45b is relatively large in area when compared with the usual small diameter circular whisker opening. Moreover, the ratio of the length of the periphery of each of the openings 45–45b to the outside diameter of the outer tube 15 in this embodiment is about 2.33 to 1. The cutting edges 47, 49 and 53 may be straight or beveled as desired. In the illustrated embodiment, the cutting edges 47 are straight as shown in FIG. 5, and the cutting edges 49 and 53 are beveled to slope downwardly as they extend inwardly when the outer tube 15 is oriented with the opening 45a facing directly upwardly. However, whether or not the cutting edges 47 and 49 are beveled, the sides of the openings 45-45b defined by the cutting edges 47 and 49 are parallel as viewed in FIG. 3.

Although the inner tube 17 can be of various different constructions, in this embodiment, it includes a cylindrical, peripheral wall 71 and a hemispherical end wall 73 at the distal end of the inner tube. The inner tube 17 has a passage 75 which extends from a proximal end 77 (FIG. 2) of the inner tube all the way to the end wall 73.

The inner tube 17 has an opening 79 and a cutting edge 81 extending along the periphery of the opening 79 and completely circumscribing the opening. The cutting edge 81 can be of any configuration that will appropriately cooperate with the cutting edges 47, 49 and 53 to shear material to be cut in a scissors-like fashion while crowding such material generally toward one of the axial cutting edges 53. In this embodiment, the opening 79 and the cutting edge 81 are generally oval, and more specifically, are generally elliptical as shown in FIG. 3. As shown in FIG. 4, the cutting edge 81 and, therefore, the opening 79 are in both the peripheral wall 71 and the end wall 73. The cutting edge 81 appears elliptical as viewed in FIG. 3 and forms an arc as shown in FIG. 4 which lies entirely above a central longitudinal axis 82 of the inner tube 17.

The opening 79 can be of various other configurations, including a configuration which matches the configuration of the openings 45-45b of the outer tube 15. If desired, an appropriate cutting edge may be provided on a non-tubular rotatable member, such as a helix, in lieu of on the inner tube 17.

In use of the cutting instrument 11, it is inserted through an opening in the knee to a region, such as the synovial tissue, which is to be cut, and the motor 19 is energized to begin unidirectional rotation of the inner tube 17 within the outer tube 15. This moves the cutting edge 81 along the cutting edges 47 and 49 of each of the openings 45-45b as generally illustrated in FIG. 6 to provide shearing or scissors-like cutting along all of the cutting edges 47 and 49 while crowding material toward the short axial cutting edges 53. This provides a reliable and effective cutting of the material along the cutting edges 47 and 49 in a way that consistency and cutting efficiency are enhanced. However, the cutting action along the cutting edges of the openings 45-45b is out of phase with each other, i.e., the cutting edge 81 at any one instant is in a different relative position with respect to each opening 45-45b as shown in FIG. 6. Because the openings 45-45b are symmetrical about the axis 51, the inner tube 17 can be rotated in either direction within the outer tube 15, and the same desirable cutting action is achieved. In addition, the outer tube 15 may be moved longitudinally such that the edges 47 and 49 provide a curetting-type of action for cutting and scraping material. Suction is applied through the passage 21, the opening 35 and the passage 75 of the inner tube 17 so as to remove severed material after it is cut so that the cutting instrument need not be withdrawn from the incision to accomplish this.

FIGS. 7-10 show a cutting instrument 111 which is identical to the cutting instrument 11 in all respects not shown or described herein. Portions of the cutting instrument 111 corresponding to portions of the cutting instrument 11 are designated by reference characters increased by 100 over those employed for the cutting instrument 11.

The primary difference between the cutting instruments 11 and 111 is in the configuration of the openings 145 and 145a. Each of the openings 145 and 145a is identical, and in this embodiment, the opening 45b is eliminated. The openings 145 and 145a have parallel cutting edges 149 of the same length, orientation and configuration as the cutting edges 49, except that the cutting edges 149 in this embodiment, are not beveled. Thus, the cutting edges 149 are straight as viewed in a particular direction, i.e., a top plan view (FIG. 7) looking straight down on the openings 145 and 145a.

Each of the openings 145 and 145a also has a curved cutting edge 83 which is part oval as viewed in FIG. 7 and which intersects the opposite ends of the associated cutting edge 149 to form corners 85. Accordingly, the cutting edges 83 and 149 define the full periphery of the associated opening 145 and 145a. The opening 145a is located entirely in the peripheral wall 137, and the opening 145 is located primarily in the peripheral wall and partly in the end wall 139.

Each of the openings 145 and 145a may be visualized as formed by intersecting planes which intersect on one side of the axis 151 to form the cutting edges 83 and 149. These cutting planes enter the outer tube 115 from such one side, and the intersection of the planes forms the corners 85. In actual practice, the openings 145 and 145a may be formed by rotating cutting tools (not shown), and thus reference herein to formation of the openings with planes is only for purposes of visualization of the opening geometry and does not refer to the process of cutting the openings or to whether or not the edges may be beveled.

The openings 145 and 145a may have the same circumferential extent as the openings 45-45b. In the embodiment of FIGS. 7-10, the ratio of the length of the periphery of each of the openings 145-145a to the outside diameter of the outer tube 115 is about 3.38 to 1.

The operation of the cutting instrument 111 is essentially as described above for the cutting instrument 11. In this regard, the shearing or scissors action proceeds along the cutting edges 83 and 149 toward the corners 85 by virtue of the cooperation between the cutting edges 83 and 149 and the cutting edge 181. The material being cut tends to be trapped in the corner 85 and is prevented from escaping. The shearing action terminates essentially simultaneously along the cutting edges 83 and 149 at the corner 85 of the opening 145; whereas, with the opening 145a, the shearing action along the cutting edge 149 is complete slightly before the completion of the shearing action along the cutting edge 83.

Although exemplary embodiments of the invention have been shown and described, many changes, modifications and substitutions may be made by one having ordinary skill in the art without necessarily departing from the spirit and scope of this invention.

We claim:

1. A surgical cutting instrument comprising:
   an outer tube sized for insertion through an opening in a patient, said outer tube having a peripheral wall and a longitudinal axis;
   said outer tube having a plurality of openings arranged generally longitudinally along the outer tube;
   each of said openings having first and second cutting edges defining portions of the periphery of such opening, said first cutting edge of each of said openings being substantially straight as viewed in a particular direction perpendicular to the longitudinal axis of the outer tube;

an inner cutting member rotatable within said outer tube;

said inner cutting member having a cutting edge cooperable with said first and second cutting edges of said openings of the outer tube for cutting material from within the patient with a shearing action that progresses along said first and second cutting edges as the inner cutting member rotates; and each of said openings including a curved edge which includes said second edge and each of said first edges intersecting the associated curved edge and substantially defining therewith the full periphery of the associated opening.

2. An instrument as defined in claim 1 wherein said first edge of said first opening extends circumferentially of said outer tube at an acute angle relative to a radial plane.

3. An instrument as defined in claim 1 wherein said first opening extends circumferentially of the outer tube for at least about 90 degrees.

4. An instrument as defined in claim 3 wherein said first edge of said first opening extends circumferentially of said outer tube at an acute angle relative to a radial plane.

5. An instrument as defined in claim 1 wherein the peripheral wall of said outer tube is generally cylindrical and has an outside diameter and the ratio of the length of said periphery of said first opening to said diameter is at least about 1.5 to 1.

6. An instrument as defined in claim 5 wherein said first edge of said first opening extends circumferentially of said outer tube at an acute angle relative to a radial plane.

7. An instrument as defined in claim 6 wherein said openings are substantially identical.

8. An instrument as defined in claim 1 wherein each of said first edges of said openings defines a proximal edge of the associated opening.

9. An instrument as defined in claim 1 wherein said inner cutting member includes an inner tube rotatable within said outer tube and having an opening therein, and said cutting edge of said inner tube extends along the periphery of the opening in the inner tube.

10. An instrument as defined in claim 9 wherein said opening in said inner tube is generally oval.

11. An instrument as defined in claim 1 including a handle, a motor carried by the handle, means for mounting the outer tube on the handle and means for coupling the inner cutting member to the motor so that the motor can rotate the inner cutting member.

12. An instrument as defined in claim 1 wherein each of said first edges extends circumferentially of said outer tube at an acute angle relative to a radial plane, each of said curved edges is part oval as viewed in said particular direction, said openings are substantially identical, the peripheral wall of said outer tube is generally cylindrical and has an outside diameter and the ratio of the length of each of said peripheries of said openings to said diameter is about 2 to 1.

13. A surgical cutting instrument comprising:

an outer tube sized for insertion through an opening in a patient, said outer tube having a peripheral wall and a longitudinal axis;

said outer tube having an opening, said opening having first and second cutting edges defining portions of the periphery of the opening, said first cutting edge of said opening being substantially straight as viewed in a particular direction perpendicular to the longitudinal axis of the outer tube;

said second cutting edge being curved and intersecting the first edge to define the full periphery of the opening;

an inner cutting member rotatable within said outer tube; and said inner cutting member having a cutting edge cooperable with said first and second cutting edges of said opening of the outer tube for cutting material from within the patient with a shearing action that progresses along said first and second cutting edges as the inner cutting member rotates.

14. An instrument as defined in claim 13 wherein said first edge extends circumferentially of said outer tube at an acute angle relative to a radial plane.

15. An instrument as defined in claim 13 wherein said opening extends circumferentially of the outer tube for at least about 90 degrees.

16. An instrument as defined in claim 13 wherein said inner cutting member includes an inner tube rotatable within said outer tube and having an opening therein, and said cutting edge of said inner tube extends along the periphery of the opening in the inner tube.

17. An instrument as defined in claim 16 wherein said opening in said inner tube is generally oval.

18. An instrument as defined in claim 13 including a handle, a motor carried by the handle, means for mounting the outer tube on the handle and means for coupling the inner cutting member to the motor so that the motor can rotate the inner cutting member.

19. An instrument as defined in claim 13 wherein said opening is formed at least in part by first and second planes which intersect on one side of said axis and form the first and second cutting edges, respectively, said first plane and said second plane enter the outer tube from said one side and the intersection of said planes forms a corner.

* * * * *